United States Patent [19]

Usami et al.

[11] Patent Number: 4,902,400
[45] Date of Patent: Feb. 20, 1990

[54] GAS SENSING ELEMENT

[75] Inventors: Jun Usami, Aichi; Akinobu Hattori, Yokkaichi; Takeshi Kajita, Aichi, all of Japan

[73] Assignee: NGK Insulators, Ltd., Nagoya, Japan

[21] Appl. No.: 30,050

[22] Filed: Mar. 25, 1987

[30] Foreign Application Priority Data

Mar. 28, 1986 [JP] Japan .................................. 61-71729

[51] Int. Cl.$^4$ ............................................. G01N 27/46
[52] U.S. Cl. ..................................... 204/426; 204/408; 204/425; 204/427
[58] Field of Search .......... 204/425, 426, 424, 427–429

[56] References Cited

U.S. PATENT DOCUMENTS

| | | | |
|---|---|---|---|
| 3,546,086 | 12/1970 | Sayles | 204/427 |
| 3,607,701 | 9/1971 | Wheeler | 204/427 |
| 4,300,990 | 11/1981 | Maurer | 204/426 |
| 4,450,065 | 5/1984 | Yamada et al. | 204/426 |
| 4,502,939 | 3/1985 | Holfelder et al. | 204/426 |
| 4,505,807 | 3/1985 | Yamada | 204/426 |
| 4,510,036 | 4/1985 | Takeuchi | 204/426 |
| 4,559,126 | 12/1985 | Mase et al. | 204/426 |
| 4,579,643 | 4/1986 | Mase et al. | 204/426 |
| 4,670,128 | 6/1987 | Mase et al. | 204/426 |
| 4,722,779 | 2/1988 | Yamada et al. | 204/426 |
| 4,755,274 | 7/1988 | Mase et al. | 204/426 |
| 4,798,693 | 1/1989 | Mase et al. | 204/425 |

OTHER PUBLICATIONS

Laid Open Publication No. 58-124943, (Japanese Patent Application No. 57-6846).

Primary Examiner—T. Tung
Attorney, Agent, or Firm—Arnold, White & Durkee

[57] ABSTRACT

A gas sensing element having a co-fired laminar structure including an electrochemical cell having a planar solid electrolyte body, and at least two electrodes disposed on the planar solid electrolyte body. The sensing element further includes two generally planar heaters which are formed on opposite sides of the electrochemical cell, respectively, and which are spaced apart from each other in a direction perpendicular to the planar solid electrolyte body, and a generally planar thermosensitive portion formed as an integral part of the laminar structure, for detecting a temperature of the laminar structure in the neighborhood of at least one of the electrodes of the electrochemical cell. The thermosensitive portion may partially define a diffusion chamber into which a measurement gas in an external space is introduced under a predetermined diffusion resistance, so that one of the electrodes is exposed to the introduced measurement gas.

7 Claims, 2 Drawing Sheets

GAS SENSING ELEMENT

BACKGROUND OF THE INVENTION

1. Field of the Invention

The present invention relates generally to an element for sensing gases, and more particularly to a gas sensing element which provides significantly improved sensing accuracy and which is suitably used as an instrument for analyzing gases.

2. Discussion of the Prior Art

There has been known a gas sensor which utilizes an ion-conductive solid electrolyte, to measure the concentration (partial pressure) of a given component in an object atmosphere or measurement gas, according to the principle of a concentration cell. For example, an oxygen sensor for determining the concentration or partial pressure of oxygen in a measurement gas, employs zirconia or similar solid electrolyte materials which exhibit relatively high oxygen-ion conductivity at an elevated temperature. For detecting the concentration of water (partial pressure of water vapor), a sensor uses a solid electrolyte material such as cerium or strontium oxides, which are hydrogen-ion conductive at an elevated temperature. Also known is a sensor which uses $\beta$-alumina ($Na_2O.11Al_2O_3$) or similar solid electrolyte materials exhibiting sodium-ion conductivity at a high temperature, for measuring the concentration or partial pressure of sulfur dioxide, by utilizing an electrochemical reaction between sodium and sulfur.

Such electrochemically operating gas sensors utilizing a solid electrolyte are used, for example, as oxygen sensors for determining the oxygen concentration in exhaust gases emitted from an internal combustion engine of a motor vehicle, or from industrial furnaces, boilers and similar equipment. The solid electrolyte of such oxygen sensors conventionally used is generally formed as a tubular body which is closed at its one end. In recent years, there has been an increasing trend toward using an elongate planar solid electrolyte body, for easier manufacture, reduced production cost, and increased compactness of the sensors. Such oxygen sensors are formed as a laminar structure having electrodes suitably disposed in contact with the planar solid electrolyte body, such that the electrodes and the solid electrolyte cooperate to constitute an electrochemical cell.

For accurate and reliable operation of the gas sensors even while the temperature of a gas to be measured is relatively low, it is necessary to use a suitable heater for holding the electrodes and solid electrolyte body of the electrochemical cell at a relatively high operating temperature. For example, a heater is disposed in the neighborhood of the electrochemical cell, so as to heat the cell via another solid electrolyte layer or other layer, or disposed in the same plane as, but spaced apart from, the electrodes. Another heater arrangement is disclosed in Japanese Patent Application No. 57-6846 (corresponding to Japanese Laid-Open Publication No. 58-124943 and U.S. Pat. No. 4,510,036), wherein a heater layer is formed over the electrodes of the electrochemical cell via a suitable electrically insulating layer, to heat the electrodes and the underlying portion of the solid electrolyte body. This type of heater arrangement permits reduced size and electric power consumption of the sensor, and relatively rapid heating of the cell.

In the gas sensors discussed above, the concentration of a given component in the object measurement gas is generally determined based on an electromotive force detected by the sensing element, according to the Nernst equation. To assure accurate measurement of the concentration of the desired component, the temperature of the gas sensor must be known. In other words, the sensor must be heated to a known temperature. Conventionally, the temperature of the sensor is considered to be equal to the temperature of the measurement gas, which is detected by a suitable temperature detector such as a thermocouple or thermoelectric thermometer. Such a temperature detector or thermometer is disposed separately from the sensor, more precisely, from its sensing element having the electrochmical cell.

An extensive study and experiment by the inventors revealed a difference between the temerature of the gas sensor and the temperature of the measurement gas. Namely, there may arise an appreciable difference between these temperatures, due to rapid changes in the temperature, flow rate and direction of the measurement gas, and other parameters. The sensor tends to have a temperature gradient in the direction of thickness of the sensor, i.e., in the direction in which the constituent layers are superposed on each other. Therefore, the temperature of the measurement gas detected by a temperature detector positioned near the sensor does not precisely represent the operating temperature of the sensing element of the gas sensor. Accordingly, it is difficult to adequately control the heater based on the temperature measured by such a temperature detector. A research by the inventors showed a temperature difference as large as between $+3.5\%$ and $-3.5\%$.

SUMMARY OF THE INVENTION

It is accordingly an object of the present invention to provide a gas sensing element having a heater which is adequately controlled so as to permit accurate measurement of a gas, without being influenced by external parameters.

The above object may be achieved by a gas sensing element of a co-fired laminar structure constructed according to the present invention, which comprises (a) at least one electrochemical cell, each of which includes a planar solid electrolyte body, and at least two electrodes disposed on the planar solid electrolyte body, (b) a first and a second, generally planar heater for heating the electrochemical cell or cells, and (c) generally planar thermosensitive means incorporated in the laminar structure. The first and second heaters are formed on opposite sides of the electrochemical cell or cells, respectively, and are spaced apart from each other in a direction perpendicular to a plane of the planar solid electrolyte body. The generally planar thermosensitive means are adapted to detect a temperature of the laminar structure in the vicinity of the electrochemical cell or cells.

In the gas sensing element of the present invention constructed as described above, the thermosensitive means having a generally planar configuration incorporated in the laminar structure of the sensing element is adapted to detect the temperature of the laminar structure in the vicinity of at least one of the electrodes of the electrochemical cell or cells of the sensing element, which is heated by the first and second generally planar heaters that are provided on both sides of the cell or a laminar assembly of the cells. In this arrangement, the temperature of the sensing element, more precisely, the temperature of the electrochemical cell or cells, can be exactly measured by the thermosensitive means, whereby the heating by the two heaters can be controlled based on the detected temperature, so as to maintain a desired temperature throughout the sensing element, in the direction of lamination of the laminar structure. Thus, the sensing accuracy of the present gas sensing element is remarkably improved.

In particular, the thermosensitive means if positioned near the electrodes of the electrochemical cell permits the temperature of the electrodes to be precisely regulated according to the detected temperature. In this case, the maximum measuring error of the sensing element is lowered to plus or minus 1%, and the sensing element may be used as a precision analyzing instrument.

According to one advantageous feature of the invention, the sensing element further comprises means for defining a diffusion chamber into which the measurement gas diffuses from the external space under a predetermined diffusion resistance, so that one of the electrodes of the sensing element is substantially exposed to the introduced measurement gas within the diffusion chamber. The diffusion chamber may or may not be filled with a porous layer or layers, either entirely or partially. In one form of this feature of the invention, the generally planar thermosensitive means partially defines the diffusion chamber.

In the case where the sensing element having such a diffusion chamber is used to measure exhaust gases which are produced as a result of combustion of a fuel-rich air-fuel mixture, unburned components or incombustibles contained in the exhaust gases react with oxygen which has been introduced into the diffusion chamber by an oxygen pumping action of the electrochemical cell. As a result of the reaction, the temperature in the diffusion chamber rises, resulting in adversely changing the temperature distribution in the sensing element if the thermosensitive means were not provided. In other words, this inconvenience is effectively eliminated or avoided according to the invention wherein the heaters are controlled based on the temperatures monitored by the generally planar heat-sensitve means which is disposed within the diffusion chamber or near this chamber, and in the vinicity of the electrode or electrodes of the cell. Thus, the provision of the thermosensitive means assures a substantially and constant temperature distribution of the sensing element.

It is preferred that the thermosensitive means be provided in the form of a layer covering a relatively large area in the plane parallel to the plane of the planar solid electrolyte body, for more uniform temperature distribution of the diffusion chamber, and the detecting portion of the sensing element which constitutes the electrochemical cell or cells. This arrangement makes it possible to reduce an offset amount of the sensing element as a concentration cell, and improve the temperature distribution within the diffusion chamber, thereby maintaining a substantially constant rate of diffusion of the measurement gas through the diffusion chamber, without being affected by the ambient temperature, and consequently enhancing the measuring accuracy of the sensing element.

Unlike the conventionally used thermocouple or other detectors which measures the temperature at a selected point, the generally planar thermosensitive means of the instant sensing element is adapted to detect the temperature over a relatively wide area, for increased detecting accuracy. Further, where the thermosensitive means is provided in or near the diffusion chamber, the thermosensitive means senses the temperature of the sensing element between the first and second heaters. This feature is effectively combined with the generally planar configuration of the thermosensitive means, contributing to further improvements in the temperature distribution and measuring accuracy.

In one preferred form of the above feature of the invention wherein the diffusion chamber is provided, the sensing element includes two electrochemical cells, that is, an electrochemical pumping cell disposed on one side of the diffusion chamber, and an electrochemical sensing cell disposed on the other side of the diffusion chamber. The pumping cell is adapted to perform an oxygen pumping action for controlling an atmosphere within the diffusion chamber, while the sensing cell is adapted to induce an electromotive force representative of a difference in oxygen concentration between the controlled atmosphere within the diffusion chamber, and a reference gas, according to the principle of an oxygen concentration cell.

According to another advantageous feature of the invention, each of the first and second generally planar heaters is a multi-layered structure including a heat generating element, and an electrically insulating layer in which the heat generating element is embedded. In this arrangement, the heat generating element is electrically insulated from the planar solid electrolyte body by the electrically insulating layer.

In one form of the above feature of the invention, the multi-layered structure of each heater further includes a gas-tight layer which covers the electrically insulating layer and thereby isolates the heat generating element from the external measurement gas. This gas-tight layer is provided since the electrically insulating layer is generally gas-permeable.

In accordance with a further feature of the invention, the generally planar heat-sensitive means is a multi-layered structure including an electrically resistive thermosensitive element, and an electrically insulating layer in which the thermosensitive element is substantially embedded. In this case, the electrically resistive thermosensitive element as a temperature detector element, is electrically insulated from the planar solid electrolyte body by the electrically insulating layer.

In connection with the electrically insulating layers indicated above, it is noted that the solid electrolyte body becomes a semi-conductor and its electrical insulating property is reduced, when its temperature reaches 450° C. In this sense, the electrically insulating layer which separates the heat generating or thermosensitive element from the solid electrolyte body is useful for avoiding otherwise possible short-circuiting of the patterns of the heating generating or thermosensitive element, which occur via the solid electrolyte body in a semi-conductive state at an elevated temperature. The electrically insulating layer may be a thin layer which principally consists of alumina or similar insulating materials.

In one form of the above feature of the invention, the multi-layered heat-sensitive structure further includes a gas-tight layer which covers the electrically insulating layer and thereby isolates the electrically resistive element from the external measurement gas. The provision of this gas-tight layer is significant, since electrically insulating materials are generally gas-permeable. Preferably, the gas-tight layer is formed of a ceramic material which has substantially the same chemical composition as that of the solid electrolyte body.

BRIEF DESCRIPTION OF THE DRAWINGS

The above and other objects, features and advantages of the present invention will become more apparent by reading the following detailed description of preferred embodiments of the invention, when considered in connection with the accompanying drawings, in which.

DETAILED DESCRIPTION OF THE PREFERRED EMBODIMENTS

To further clarify the concept of the present invention, some preferred embodiments of the invention will be described in detail, by reference to the accompanying drawings.

Figure 1:
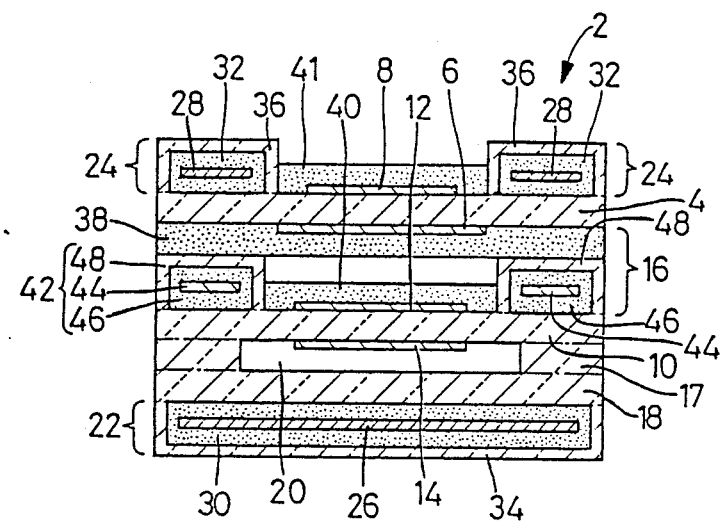
FIG. 1 through FIG. 4 are elevational views in transverse cross section of detecting portions of different embodiments of a gas sensing element of the invention, in the form of oxygen sensing elements, respectively.

Referring first to FIG. 1, there is shown in transverse cross section an oxygen detecting portion of an oxygen sensing element 2, which is one form of a gas sensing element constructed according to the invention. This oxygen sensing element 2 has a generally elongate planar configuration having a generally rectangular transverse cross sectional shape. On one of opposite longitudinal ends of the element 2, there is formed the oxygen detecting portion having an electrochemical cell which is operable according to the principle of an oxygen concentration cell.

As indicated in the figure, the oxygen detecting portion of the sensing element 2 has a co-fired laminar structure, which includes an electrochemical pumping cell and an electrochemical sensing cell. The pumping cell consists of a first planar solid electrolyte body 4 made of stabilized zirconia that exhibits oxygen-ion conductivity at a high temperature, and an inner and an outer porous pumping electrode 6, 8 which are formed on the opposite major surfaces of the solid electrolyte body 4. Similarly, the sensing cell consists of a second planar solid electrolyte body 10, and porous measuring and reference electrodes 12, 14 which are formed on the opposite major surfaces of the second solid electrolyte body 10. Between these electrochemical pumping and sensing cells, there is formed a diffusion chamber 16 which will be described. On one side of the sensing cell on which the reference electrode 14 is disposed, third and fourth planar solid electrolyte bodies 17, 18 are superposed, such that these two bodies 17, 18 cooperative with the second solid electrolyte bodies 10 to define an air passage 20 in which the reference electrode 14 is accommodated. This air passage 20 is open to the ambient air, at its end remote from the oxygen detecting portion, for introducing the air as a reference gas to which the reference electrode 14 is exposed.

Stabilized zirconia of the solid electrolyte bodies 4, 10, 17 and 18 is obtained by doping zirconium oxide with yttrium oxide or calcium oxide, as well known in the art. The electrodes 6, 8, 12 and 14 are formed of platinum or similar metals.

On the outer surface of the fourth solid electrolyte body 18 remote from the air passage 20, there is formed a first heater 22 in the form of a planar multi-layered structure. Further, a second heater 24 also in the form of a planar multi-layered structure is formed on the outer surface of the pumping cell, so as to surround the outer pumping electrode 8 in the plane of FIG. 1. Thus, the two generally planar heaters 22 and 24 are provided on the opposite sides of a laminar assembly of the pumping and sensing cells, such that the two heaters 22, 24 are spaced from each other in the direction perpendicular to the plane of the solid electrolyte bodies 4, 10. These heaters 22, 24, which are integral parts of the laminar structure of the sensing element 2, are operated to heat the two electrochemical cells to a predetermined optimum operating temperature. Each of the first and second heaters 22, 24 includes a heat generating element 26, 28, an electrically insulating porous layer 30, 32 formed of alumina or similar ceramic material so as to surround the heat generating element 26, 28, and a gas-tight layer 34, 36 formed of zirconia or other solid electrolyte material. The gas-tight layer 34, 36 cooperates with the solid electrolyte body 18, 4 to enclose the heat generating element 26, 28 and the insulating layer 30, 32, and thereby isolates the heat generating element 26, 28 from an external atmosphere to be measured by the sensing element 2. The heat generating elements 26, 28 of the first and second heaters 22, 24 are formed, for example, from a cermet film whose major components consist of a powdered mixture of alumina and platinum.

The inner pumping electrode 6 and the measuring electrode 12 are exposed to the atmosphere within the diffusion chamber 16 through respective porous ceramic layers 38, 40 made of alumina or similar ceramic materials. The porous ceramic layer 38 is exposed at its lateral end faces to the external measurement gas. In this arrangement, the measurement gas diffuses into the diffusion chamber 16 through the porous ceramic layer 38, under a predetermined diffusion resistance of the layer 38, and the inner pumping electrode 6 and the measuring electrode 12 are exposed to the introduced measurement gas within the diffusion chamber 16. A similar porous ceramic layer 41 is formed so as to cover the outer pumping electrode 8.

Between the porous ceramic layer 38 and the second planar solid electrolyte body 10, there is disposed a generally planar multi-layered thermosensitive means 42, such that the thermosensitive means cooperates with the first and second solid electrolyte bodies 4, 10 to define the diffusion chamber 16 which accommodates the ceramic layers 38, 40. More specifically, the thermosensitive means 42 is formed so as to surround the measuring electrode 12, and positioned adjacent to the inner pumping electrode 6. The thermosensitive means 42 includes an electrically resistive thermosensitive element 44 in the form of a thermistor whose resistance decreases as the temperature increases. The multi-layered structure of the thermosensitive means 42 further includes an electrically insulating porous layer 46 made of alumina or similar ceramic material. The electrically resistive thermosensitive element 44 is embedded in the electrically insulating porous layer 46, and is thereby electrically insulated from the solid electrolyte body 10. The thermosensitive element 44 is isolated or protected from the external measurement gas, and from the internal measurement gas within the diffusion chamber 16, by a gas-tight layer 48 made of zirconia or other solid electrolyte material similar to the solid electrolyte body (10). The electrically resistive thermosensitive element 44 which is formed in a film, is made for example, of a cermet principally consisting of a powdered mixture of a ceramic material such as zirconia or alumina, and platinum. Alternatively, the resistive element 44 may be made of a cermet containing 0.1–0.5% of $TiO_2$ (titania), or other materials which positively give the thermosensitive film 44 a high negative temperature coefficient of resistance.

The laminar structure of the oxygen sensing element 2 thus constructed is prepared by co-firing the successively superposed unfired layers of the constituent protions, that is, first heater 22, solid electrolyte bodies 18, 17, sensing cell (10, 12, 14), thermosensitive means 42, portions defining the diffusion chamber 16, pumping cell (4, 6, 8) and second heater 24.

Figure 2:
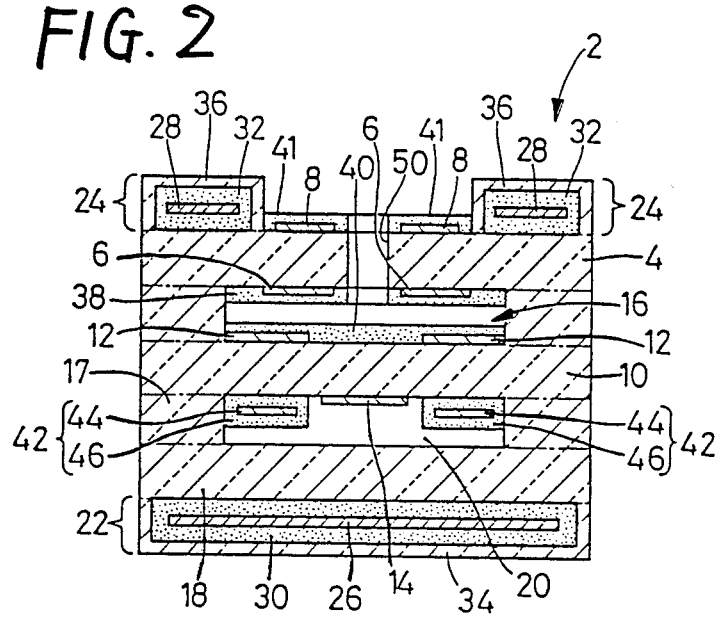

Referring next to FIG. 2, there is illustrated an oxygen sensing element 2 according to another embodiment of the present invention. This sensing element 2 is different from the element 2 of FIG. 1, in the arrangement defining the diffusion chamber 16, and the arrangement and position of the thermosensitive means 42. Described more specifically, the diffusion chamber 16 has a predetermined diffusion resistance due to its comparatively small thickness, rather than the porosity of the porous ceramic layer 38 used in the preceding embodiment. That is, the diffusion chamber 16 in the present embodiment is a thin flat space between the first and second planar solid electrolyte bodies 4, 10. Further, the pumping cell (first solid electrolyte body 4) has a gas-inlet aperture 50 which communicates with the central part of the diffusion chamber 16, so that the external measurement gas enters the diffusion chamber 16 through the aperture 50. The thermosensitive means 42 consists of an electrically resistive thermosensitive element 44, and an electrically insulating porous layer 46 surrounding the thermosensitive element 44. The thermosensitive means 42 is located within the air passage 20, adjacent to the reference electrode 14 of the sensing cell, in order to detect the temperature in the vicinity of the reference electrode 14. Since the thermosensitive means 42 provided within the air passage 20 in this embodiment is not influenced by the external measurement gas, the thermosensitive means 42 is not covered by a gas-tight layer (as indicated at 48 in FIG. 1) for isolating the thermosensitive element 44 from the external measurement gas.

In the oxygen sensing elements 2 illustrated above, an electric current is applied between the inner and outer pumping electrodes 6, 8 of the pumping cell, according to the concentration of a given component (oxygen) in the measurement gas which is introduced into the diffusion chamber 16 under a predetermined diffusion resistance. As a result, a well known oxygen pumping action is carried out by the pumping cell, to control the atmosphere in the diffusion chamber 16, adjacent to the inner pumping electrode 6. At the same time, an electromotive force is induced between the measuring and reference electrodes 12, 14 of the sensing cell, based on a difference in the oxygen concentration between the controlled atmosphere within the diffusion chamber 16 and the reference gas (air) within the air passage 20, according to the principle of an oxygen concentration cell. During this operation, the temperature of the sensing element 2, more specifically, the temperature near the inner pumping electrode 6 and the measuring electrode 12 within the diffusion chamber 16 is precisely detected by the electrically resistive thermosensitive element 44 of the thermosensitive means 42.

The heating operations of the first and second heaters 22, 24 disposed on the opposite sides of the sensing element 2 can be regulated based on the temperature of the sensing element 2, in particular, the temperature near the sensing cell, which is detected by the built-in generally planar heat-sensitive means 42. The generally planar configuration of the thermosensitive means 42 (electrically resistive element 44) permits more accurate detection of the temperature in the diffusion chamber 16 or of the electrodes 12, 14 of the oxygen concentration sensing cell, than a conventional temperature detector which is configured to measure the temperature at a selected point, rather than an area. Thus, the thermosensitive means 42 provides for improved precision of the temperature detection, and accordingly improved temperature distribution by the heating of the heaters 22, 24. In other words, the generally planar thermosensitive means 42 makes it possible to reduce the amount of offset of the concentration cell, improve the temperature distribution within the diffusion chamber 16, maintain a substantially constant rate of diffusion of the measurement gas into the diffusion chamber 16 without being affected by the ambient temperature, and thereby enhance the measuring accuracy of the sensing element 2.

Unlike the conventional temperature detector separate from the sensing element itself, the instant thermosensitive means 42 takes the form of a layer covering a relatively wide area in the plane of the sensing element 2, and monitors the temperature of that wide area, rather than the temperature at a single point. In this context, the present arrangement is advantageous for exact monitoring of the operating temperature of the sensing element which is heated by the first and second heaters 22, 24. Further, the location of the thermosensitive means 42 between the two heaters 22, 24 is also conducive to accurate control of the temperature of the sensing element 2, so as to maintain a uniform temperature distribution for more accurate measurement of the object gas.

In particular, the instant thermosensitive means 42 is effective, where the gas to be measured is an exhaust gas which is produced in combustion of an air-fuel mixture having an air-fuel ratio lower than the stoichiometric level and which contains unburned components. In this case, the unburned components introduced into the diffusion chamber 16 are burned by oxygen which has been pumped into the diffusion chamber 16 by means of an oxygen pumping action by the pumping cell. The burning of the unburned components will raise the temperature within the diffusion chamber 16. This rise of the temperature can be exactly and rapidly sensed as a change in the resistance of the electrically resistive thermosensitive element 44 of the thermosensitive means 42 disposed within or in the neighborhood of the diffusion chamber 16. Consequently, the heaters 22, 24 can be precisely controlled so as to maintain the sensing element 2 at an optimum operating temperature. Further, the thermosensitive means 42 makes it possible to deal with different kinds of measurement gases, which affects the operating temperature of the sensing element 2.

The inner pumping and measuring electrodes 6, 12 exposed to the atmosphere within the diffusion chamber 16, and the outer pumping electrode 8 directly exposed to the external measurement gas, are covered by ceramic filters in the form of the porous ceramic layers 38, 40, 41 having suitable thicknesses, whereby the durability of these electrodes 6, 8, 12 is effectively improved. Preferably, these protective porous ceramic layers 38, 40, 41 are made of a ceramic material which has a lower coefficient of thermal expansion than the solid electrolyte bodies. The porosity of the protective layers is preferably within a range of 30–50%, and the average particle size is preferably within a range of 1–5 microns.

As previously indicated, the heat generating elements 26, 28 of the heaters 22, 24, and the electrically resistive thermosensitive element 44 of the thermosensitive means 44, are embedded within or enclosed by the electrically insulating porous layers 30, 32, 46. These insulating layers protect the heat generating and thermosensitive elements 26, 28, 44 against otherwise possible short-circuiting with respect to the solid electrolyte bodies 4, 10, 18. Described in more detail, the solid electrolyte bodies become semiconductive at temperatures higher than 450° C., with their electrical insulation property being reduced. In this condition, carbon and other substances contained in the measurement gas (exhaust gases) tend to be easily deposited on the surface of the solid electrolyte, causing a short-circuiting if the electrical insulation of the heat generating and/or thermosensitive elements 26, 28, 44 is not sufficient. This undesirable phenomenon is effectively eliminated by the provision of the insulating layers 30, 32, 46, and the gas-tight layers 34, 36, 48.

Figure 3:
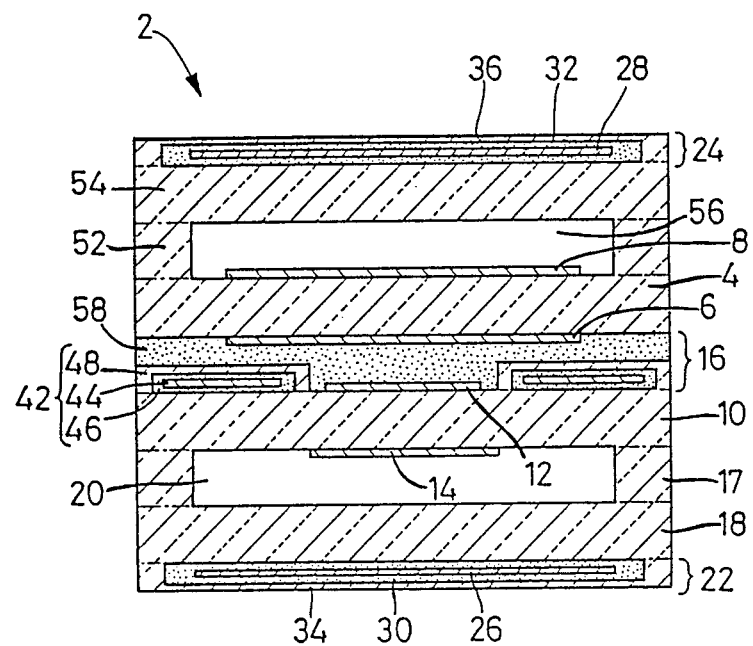

Reference is now made to FIG. 3, which shows in transverse cross section a further modified form of the oxygen sensing element according to the invention. This sensing element 2 is different from the sensing elements 2 of FIGS. 1 and 2, in that the outer pumping electrode 8 of the pumping cell is not exposed to the external measurement gas, but exposed to the atmosphere within a second air passage 56 similar to the air passage 20. The second air passage 56 is defined by the first solid electrolyte body 4, and two other solid electrolyte bodies 52, 52 superposed on the first solid electrolyte body 4. This air passage 56 is open to the ambient air, at its end remote from the oxygen detecting portion of the sensing element 2. In the present embodiment, the second multi-layered heater 24 also consisting of a heat generating element 28, a porous layer 32 and a gas-tight layer 36, is formed on the outer surface of the solid electrolyte body 54.

Further, the diffusion chamber 16 formed between the pumping cell (4, 6, 8) and the sensing cell (10, 12, 14) is entirely filled with a porous ceramic layer 58. This porous ceramic layer 58 has a predetermined diffusion resistance, so that the external measurement gas is introduced into the diffusion chamber 16 under the predetermined diffusion resistance, whereby the inner pumping electrode 6 and the measuring electrode 12 are exposed to the introduced measurement gas. The thermosensitive means 42 also consisting of an electrically resistive thermosensitive element 44, an electrically insulating layer 46 and a gas-tight layer 48, is disposed near the measuring electrode 12 so as to surround the same, and so as to partially define the diffusion chamber 16.

In the present oxygen sensing element 2, the oxygen pumping by the pumping cell consisting of the solid electrolyte body 4 and the pumping electrodes 6, 8 occurs between the second air passage 56 (in which the ambient air is introduced), and the diffusion chamber 16 (into which the measurement gas diffuses through the porous ceramic layer 58), so that the atmosphere adjacent to the measuring electrode 12 in the diffusion chamber 16 is controlled by the pumping action. In the meantime, an electromotive force is induced between the measuring and reference electrodes 12, 14 of the sensing cell, according to the principle of a concentration cell. During this operation of the sensing element 2 while being heated by the first and second heaters 22, 24, the temperature of the sensing element 2 is precisely monitored by the generally planar multi-layered thermosensitive means 42 disposed within the diffusion chamber 16. Thus, the operations of the two heaters 22, 24 are controlled based on the detected temperature, to establish a uniform temperature distribution in the direction perpendicular to the plane of the solid electrolyte bodies, whereby relatively high measuring accuracy of the sensing element 2 is assured.

Figure 4:
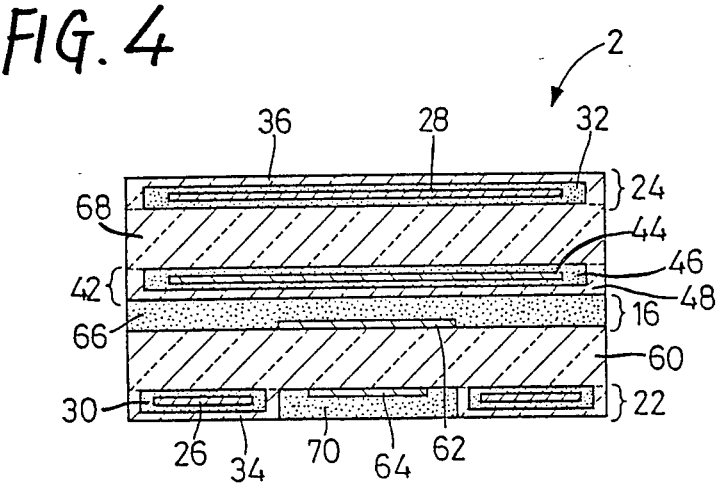

There is shown in FIG. 4 a further modified form of an oxygen sensing element 2 also according to the present invention, wherein the oxygen concentration is measured according to the principle of a polarographic cell. The sensing element 2 includes an electrochemical cell which consists of a first planar solid electrolyte body 60, and a first and a second porous electrode 62, 64 that are formed on the opposite major surfaces of the solid electrolyte body 60. On one side of this electrochemical cell, there is formed a multi-layered, generally planar first heater 22. On the other side of the cell, there are successively superposed one on another a porous ceramic layer 66 whose porous structure provides a diffusion chamber 16, a multi-layered, generally planar thermosensitive means 42, a second planar solid electrolyte body 68, and a multi-layered, generally planar second heater 24. Thus, the oxygen sensing element 2 is formed as an integral laminar structure. The second electrode 64 is is covered by a porous ceramic layer 70, so that the electrode 64 is exposed to the external measurement gas through the porous structure of the layer 70.

The thus constructed oxygen sensing element 2 is fabricated in the following manner, for example. Initially, unfired layers for the electrically insulating porous layer 32, heat generating element 28 and gas-tight layer 36 are formed by printing on one surface of a prepared unfired layer of the second solid electrolyte body 68. Then, unfired layers for the electrically insulating porous layer 46, electrically resistive thermosensitive element 44 and gas-tight layer 48 are formed by printing on the other surface of the unfired layer of the solid electrolyte body 68.

On one surface of a prepared unfired layer of the first solid electrolyte body 60, there is formed by printing an unfired layer for the first electrode 62, which serves as an inner pumping electrode. Then, an unfired layer for the porous ceramic layer 66 is formed on the same surface of the unfired solid electrolyte body 60, so as to cover the unfired inner pumping electrode 62. On the other surface of the unfired solid electrolyte body 60, there is formed by printing an unfired layer for the second electrode 64, which serves as an outer pumping electrode. Subsequently, unfired layers for the electrically insulating porous layer 30, heat generating element 28 and gas-tight layer 34 are formed by printing, so as to surround the unfired outer pumping electrode 64.

The thus prepared two unfired assemblies with the various printed unfired layers, that is, a first assembly including the unfired first solid electrolyte body 60, and a second assembly including the unfired second solid electrolyte body 68, are butted together such that the unfired layer for the porous ceramic layer 66 on the first assembly contacts the unfired layer for the gas-tight layer 48 on the second assembly. The obtained unfired laminar structure is then fired. Thus, the co-fired laminar structure of the oxygen sensing element 2 is prepared.

In the thus prepared oxygen sensing element 2, the porous ceramic layer 66 formed between the first solid electrolyte body 60 and the thermosensitive means 42 (gas-tight layer 48) practically functions as the diffusion chamber 16 having a predetermined diffusion resistance. Since the porous ceramic layer 66 is exposed to the external measurement gas at its periphery, the external measurement gas diffuses into the porous structure of the layer 66, that is, the diffusion chamber 16, so that the inner pumping electrode 62 is exposed to the atmosphere within the diffusion chamber 16. A voltage is applied between the inner and outer pumping electrodes 62, 64, to effect an oxygen pumping action. The oxygen concentration of the measurement gas is determined by measuring a limit current Ip (oxygen pumping current) which passes through the pumping cell, as well known in the art.

According to the above arrangement, the inner pumping electrode 62 is exposed to a relatively large amount of the measurement gas within the diffusion chamber 16, and an electric signal of up to 0.6 $\mu$A/ppm can be obtained, for example, where the oxygen concentration of the measurement gas is expressed in ppm. This indicates an improvement in the oxygen detecting accuracy of the sensing element 2.

The formation of the porous ceramic layer 66, i.e., the diffusion chamber 16, by a printing technique, is advantageous for accurate control of the temperature of the sensing element 2, in particular, within the diffusion chamber 16, namely, for accurate control of the first and second heaters 22, 24 based on the thermosensitive means 42. In this arrangement, too, the temperature of the sensing element 2 can be made substantially constant in the direction of thickness, assuring consistently high accuracy of measurement, even if the flow rate and temperature of the measurement gas are varied.

While the several specific oxygen sensing elements have been described as preferred embodiments of a gas sensing element of the present invention, the principle of the invention is applicable to other types of oxygen sensing elements, and other gas sensing elements, detectors or controllers that are adapted to detect components of the measurement gas, other than oxygen, such as nitrogen, carbon dioxide and hydrogen, which are associated with an electrode reaction.

It is to be understood that the invention is not limited to the precise details of the illustrated embodiments, but the invention may be embodied with various changes, modifications and improvements which may occur to those skilled in the art, without departing from the spirit and scope of the invention defined in the following claims.

What is claimed is:

1. A gas sensing element having a co-fired laminar structure, comprising:
    at least one electrochemical cell, each of which includes a planar solid electrolyte body, and at least two electrodes disposed of said planar solid electrolyte body;
    means for defining a planar diffusion chamber into which a measurement gas diffuses from an external space under a predetermined diffusion resistance;
    at least one of said at least two electrodes of said at least one electrochemical cell being substantially exposed to said measurement gas in said diffusion chamber;
    a first and a second, generally planar heater for heating said at least one electrochemical cell, said first and second heaters being formed on opposite sides of said at least one electrochemical cell, respectively, and being spaced apart from each other in a direction perpendicular to a plane of said at least one planar solid electrolyte body, each of said first and second heaters including a heat generating element, a porous electrically insulating layer in which said heat generating element is substantially embedded, and a gas-tight layer which covers said porous electrically insulating layer and thereby isolates said heat generating element from said measurement gas in said external space; and
    generally planar thermosensitive means incorporated in said laminar structure, said generally planar thermosensitive means comprising an electrically resistive thermosensitive element, and a porous electrically insulating layer in which said thermosensitive element is embedded, such that said thermosensitive element is electrically insulated from said planar solid electrolyte body, said thermosensitive element being juxtaposed in substantially the same plane as said planar diffusion chamber to detect a temperature of the laminar structure in the vicinity of said planar diffusion chamber, and providing an output for controlling power supplied to said first and second heaters.

2. A gas sensing element according to claim 1, further comprising at least one porous layer which fills at least a portion of said diffusion chamber.

3. A gas sensing element according to claim 1, wherein said generally planar thermosensitive means constitutes a part of said means for defining a diffusion chamber, and partially defines said diffusion chamber.

4. A gas sensing element according to claim 1, wherein said at least one electrochemical cell consists of an electrochemical pumping cell disposed on one side of said diffusion chamber, and an electrochemical sensing cell disposed on the other side of said diffusion chamber, said electrochemical pumping cell permforming an oxygen pumping action for controlling an atmosphere within said diffusion chamber, while said electrochemical sensing cell producing an electromotive force based on a difference in oxygen concentration between the controlled atmosphere within said diffusion chamber, and a reference gas, according to the principle of an oxygen concentration cell.

5. A gas sensing element according to claim 1, wherein said generally planar thermosensitive means further comprises a gas-tight layer which covers said porous electrically insulating layer of said thermosensitive means and thereby isolates said electrically resistive thermosensitive element from said external measurement gas.

6. A gas sensing element having a co-fired laminar structure, comprising:
    at least one electrochemical cell, each of which includes a planar solid electrolyte body and at least two electrodes disposed on said planar solid electrolyte body, one of said at least one electrochemical cell including an electrochemical sensing cell having a sensing electrode, and a reference electrode exposed to a reference gas;
    means for defining a planar diffusion chamber into which a measurement gas diffuses from an external space under a predetermined diffusion resistance, wherein; at least the sensing electrode of said electrochemical cell is substantially exposed to said measurement gas in said diffusion chamber;

a first and a second, generally planar heater for heating said at least one electrochemical cell, said first and second heaters being formed on opposite sides of said at least one electrochemical cell, respectively, and being spaced apart from each other in a direction perpendicular to a plane of said at least one planar solid electrolyte body, each of said first and second heaters including a heat generating element, a porous electrically insulating layer in which said heat generating element is substantially embedded, and a gas-tight layer which covers said porous electrically insulating layer and thereby isolates said heat generating element from said measurement gas in said external space; and generally planar thermosensitive means incorporated in said laminar structure and disposed adjacent said sensing electrode, said generally planar thermosensitive means comprising an electrically resistive thermosensitive element, and a porous electrically insulating layer in which said thermosensitive element is embedded, such that said thermosensitive element is electrically insulated from said planar solid electrolyte body, said thermosensitive element being juxtaposed in substantially the same plane as said planar diffusion chamber to detect a temperature of the laminar structure in the vicinity of said planar diffusion chamber, and providing an output for controlling power supplied to said first and second heaters.

7. A gas sensing element having a co-fired laminar structure, comprising:

at least one electrochemical cell, each of which includes a planar solid electrolyte body, and at least two electrodes disposed on said planar solid electrolyte body;

means for defining a planar diffusion chamber into which a measurement gas diffuses from an external space under a predetermined diffusion resistance;

at least one of said at least two electrodes of said at least one electrochemical cell being substantially exposed to said measurement gas in said diffusion chamber;

a first and a second, generally planar heater for heating said at least one electrochemical cell, said first and second heaters being formed on opposite sides of said at least one electrochemical cell, respectively, and being spaced apart from each other in a direction perpendicular to a plane of said at least one planar solid electrolyte body, each of said first and second heaters including a heat generating element, a porous electrically insulating layer in which said heat generating element is substantially embedded, and a gas-tight layer which covers said porous electrically insulating layer and thereby isolates said heat generating element from said measurement gas in said external space; and generally planar thermosensitive means incorporated in said laminar structure and disposed between said first and second heaters in a direction of thickness of said laminar structure of the sensing element, said generally planar thermosensitive means comprising an electrically resistive thermosensitive element, and a porous electrically insulating layer in which said thermosensitive element is embedded, such that said thermosensitive element is electrically insulated from said planar solid electrolyte body, said thermosensitive element being juxtaposed in substantially the same plane as said planar diffusion chamber to detect a temperature of the laminar structure in the vicinity of said planar diffusion chamber, and providing an output for controlling power supplied to said first and second heaters.

* * * * *